US00PP19270P3

(12) United States Plant Patent
Gerawan

(10) Patent No.: US PP19,270 P3
(45) Date of Patent: Sep. 30, 2008

(54) GRAPE PLANT NAMED 'GG-80D'

(50) Latin Name: *Vitis vinifera*
Varietal Denomination: GG-80D

(75) Inventor: Mike Gerawan, 21249 E. Jefferson, Reedley, CA (US) 93654

(73) Assignee: Mike Gerawan, Reedley, CA (US)

( * ) Notice: Subject to any disclaimer, the term of this patent is extended or adjusted under 35 U.S.C. 154(b) by 83 days.

(21) Appl. No.: 11/704,816

(22) Filed: Feb. 8, 2007

(65) Prior Publication Data

US 2008/0196131 P1 Aug. 14, 2008

(51) Int. Cl.
*A01H 5/00* (2006.01)

(52) U.S. Cl. ..... Plt./205

(58) Field of Classification Search ..... Plt./205
See application file for complete search history.

*Primary Examiner*—Annette H Para
(74) *Attorney, Agent, or Firm*—Townsend and Townsend and Crew LLP

(57) ABSTRACT

A new and distinct variety of grape plant characterized by a medium dark red seedless grape that matures for harvest and shipping in late August to September about the same time as 'Ruby Seedless' (non patented) with very good flavor, juicy and firm skin. The berries are borne on strong woody stems and branches and are well adapted to commercial handling.

1 Drawing Sheet

Latin name of the genus and species: The grape cultivar of this invention is botanically identified as *Vitis vinifera.*

Variety denomination: The variety denomination is 'GG-80D'.

BACKGROUND OF THE INVENTION

The present invention relates to a new and distinct variety of grape which will hereinafter be denominated as 'GG-80D' and more particularly as a grapevine which produces a medium size red seedless grape which is mature for harvesting and shipping in late mid-season (in normal season mid to late August). However, in 2006 maturing occurred near mid-October. The new invention resembles 'Ruby Seedless' (non patented), maturing in the same time but produces a darker red to purple berry, slightly larger and more uniform in size within the cluster.

ORIGIN AND ASEXUAL REPRODUCTION

The new variety of *Vitis vinifera* is a bud sport of 'Ruby Seedless' (non patented) which was a cross between 'Emperior' (non patented) and 'Pirovano 75' (non patented), a large seedless Italian grape made by Dr. Harold P. Olmo in 1939, selected in 1950 and introduced into trade in 1968. 'Ruby Seedless' has been grown in the San Joaquin Valley of Central California for the past three decades. This bud sport of 'Ruby Seedless' has been observed in 2004 and was grafted on two mature vines in a block of 'Ruby Seedless' in the dormant season of that year producing flowers, inflorescence, and berries in 2005. The resulting berry—medium, dark red to purple—displays uniformity in size and is very sweet. The 'GG-80D' has been shown to maintain its distinguishing characteristics throughout and during asexual propagation done in the San Joaquin Valley of Central California.

The cultivar is stable and reproduces true to type in successive generations of asexual reproduction.

BRIEF SUMMARY OF THE INVENTION

The 'GG-80D' grapevine is characterized by producing a medium dark red grape with a very good flavor and good productive capacity that matures for harvesting and shipment in late mid-season on the west side of Madera Avenue which is located on the west side of the San Joaquin Valley approximately 18 miles west of Fresno, Calif. The new variety can be compared to 'Ruby Seedless' but produces a slightly larger dark red berry with very good flavor.

DETAILED DESCRIPTION OF THE INVENTION

Figure 1:
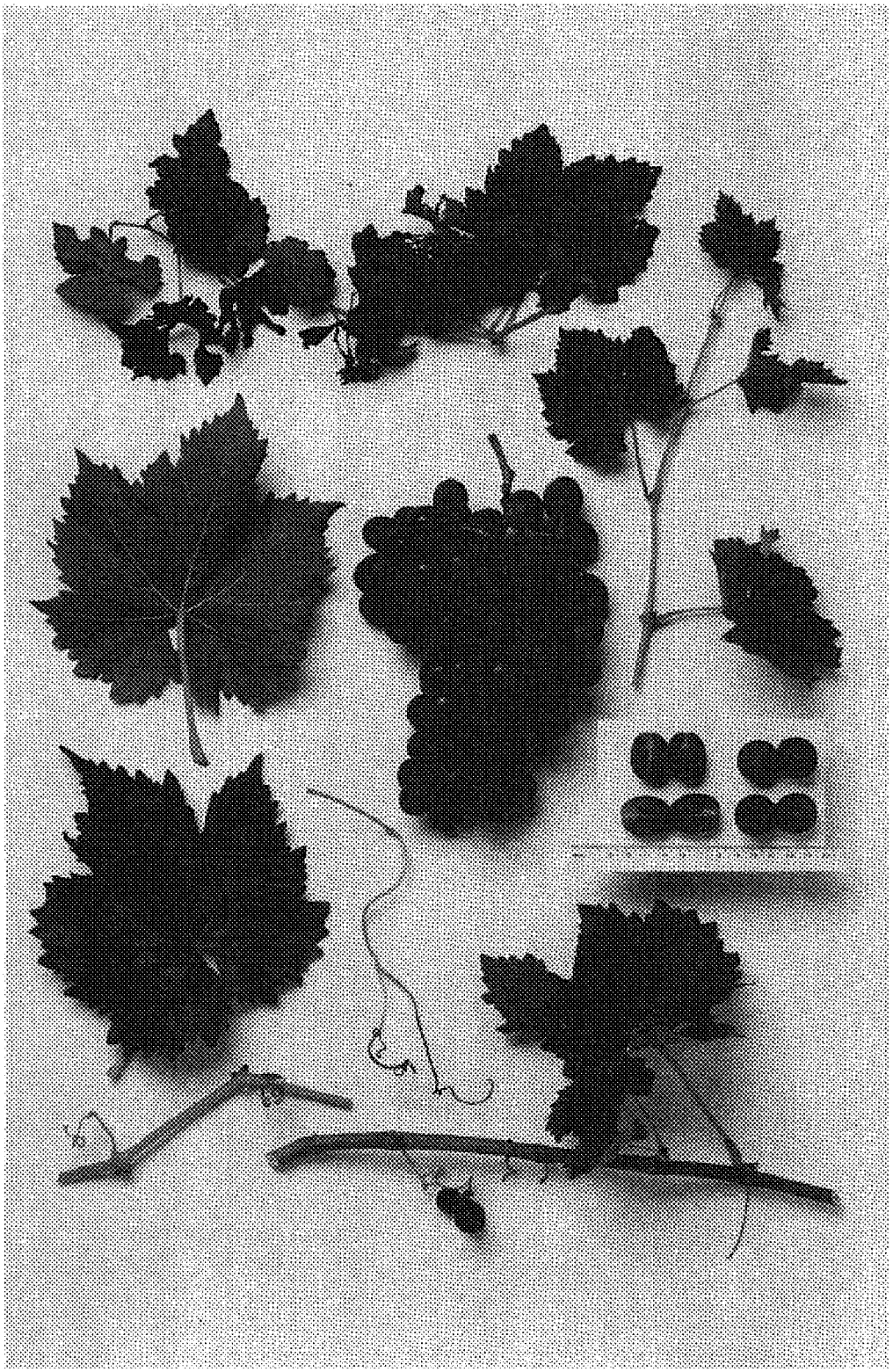
FIG. 1 shows across the top, small leaves with a terminal shoot and a leaf cluster and nodes with leaves, just below on the left is a mature leaf displaying the underside; along side is a mature berry cluster and to the right is a terminal shoot and small leaves; just below the shoot are 4 berries cut in half—2 longitudinal and 2 horizontally—displaying the flesh. Just below on the left is a mature leaf upper side with a long continuous tendril on the left. On the bottom is a piece of immature branch and tendrils with a mature cane with nodes, tendrils, young leaves and several late season berries.

Referring more specifically to the horticultural description of the 5 year old new and distinct variety of grapevine, the following description has been observed under the ecological conditions prevailing at the origin vineyard which is located on the west side of the San Joaquin Valley of Central California. All major color descriptions are by reference to the Dictionary of Color by Maerz & Paul, First Edition, published in 1930. Common colors are also employed.

Vine:

*Generally.*—Large.
*Vigor.*—Very good.
*Figure (form).*—With wide cordons forming a 'T' shape.
*Production.*—Very good.
*Regularity of bearing.*—Regular.

Trunk:
*Size.*—Large — 24 inches (69.6 cm) in circumference; 21 inches (53.4 cm) above ground.
*Surface.*—Texture — rough, shaggy.
*Color.*—Bark — Pl.7 C8 Mauve Taupe.
*Mature cane.*—Pl.13 L9 — Chipmunk.
*Nodes.*—6 nodes on 14½ inches of cane (36.83 cm).
*Length between nodes.*—2½-3 inches (6.25-7.62 cm).
*Lenticel.*—0.
*Lenticels size.*—0.
*Shoots.*—Size — moderate.
*Shoots.*—Length — medium — 3-5 inches (7.62-12.7 cm).
*Shoots shape.*—Semi-droopy.
*Tendrils.*—Number — consecutive up to two.
*Tendrils.*—Size — medium — 4 inches (10.16 cm).
*Tendrils.*—Location — at nodes.
*Tendrils form.*—Bifurcate.
*Tendrils.*—Texture — firm.
*Bud shape.*—Convex.
*Buds.*—Size — 7 mm (0.28 inch) wide and 10 mm (0.39 inch) long.
*Buds fruitfulness.*—Very good.
*Bud break date.*—N/A.

Branches:
*Size.*—Medium — 2 inches (5.08 cm) in circumference.
*Cordon.*—46 inch (116.55 cm) on side of vine trans; 53 inch (134.62 cm) on the other side of the trunk.
*Color.*—One year of older wood Pl.13 L9 Chipmunk.
*Color.*—Immature branch — Pl.19 K6 Sea Green.

Leaves:
*Size.*—Medium to large.
*Density.*—Dense.
*Average length.*—Average 19.7 cm (7.70 inch).
*Average width.*—13.31 cm (5.240 inch).
*Form.*—Pentagonal.
*Texture.*—Upper surface — smooth.
*Texture.*—Lower surface — slightly glabrous.
*Color.*—Upwardly disposed surface — Pl.23 J11 Cossack Green.
*Color.*—Downwardly disposed surface — Pl.22 L9 — Near Brunswick gr. LT.
*Color.*—Leaf Vein — Pl.19 L6 Calliste gr.
*Marginal form.*—Tooth.
*Leaf vein.*—Thickness — 4 mm (0.16 inch) — generally undulate.
*Margin.*—Generally undulate.
*Petiole size.*—Medium.
*Petiole length.*—3-4 3/16 inches (7.62-11.12 cm).
*Petiole thickness.*—4-5 mm (0.16-0.20 inch).
*Petiole color.*—Pl. 19 L6 Calliste gr.
*Petiole sinus.*—Form — upside down U-shape.
*Lobes.*—4.
*Tooth size.*—9 mm (0.35 inch) width — 10 mm (0.39 inch) length.
*Tooth number.*—2-3 large between Lobes.
*Tooth shape.*—Convex.

Inflorescence:
*Size.*—Large — 13.0-16.5 cm (5.2-6.50 inch).
*Number.*—Borne Per Spur — 2-3 per spur.
*Number borne per vine.*—Many.

Flowers:
*Flower buds.*—Size — small (1-2 mm).
*Flower buds.*—Surface texture — glabrous.
*Flowers.*—Generally — heavy.
*Date of bloom.*—May 16-20th.
*Date of full bloom.*—May 24th.
*Size.*—Average 5 mm (0.201 inch).
*Petals.*—Color — Pl.7 H6 — Peony & Burmese Ruby.
*Petals.*—Size — small — 1 mm (0.025 inch).
*Pistil.*—Color — Pl.17 L7 Viridine y.
*Amount of pollen.*—N/A.
*Date visible berry set.*—May 24th.
*Size.*—Small — 2 mm (0.079 inch).

Fruit:
*Solids.*—20.0.
*Acids.*—0.36.
*Sugar/acid ratio.*—55.6.
*Juice ph.*—4.71.
*Seeds.*—0.
*Seed number.*—0.
*Capstem pedicel.*—Avg. 7 mm (0.28 inch).
*Berry weight.*—7.1 grams.
*Juice color.*—Pl.1 2C Peach Blossom.
*Size.*—Medium.
*Cluster size.*—Medium.
*Cluster.*—Average length — not including mainstem — 6 inch (15.24 cm).
*Cluster.*—Average diameter — at greatest width — 6 inch (15.24 cm).
*Cluster weight.*—568 grams (1¼ lb.).
*Compactness.*—Compact.
*Cluster form.*—Conical.
*Stems.*—Generally — 2 inch (5.04 cm).
*Stems.*—Caliper — 6 mm (0.24 inch).
*Berry size.*—Medium.
*Berry form.*—Ovate.
*Berry number.*—Approximately 80.
*Berry size.*—Average dimension longitudinal axis — 25 mm (0.98 inch).
*Berry size.*—Average dimension in transverse axis — 21 mm (0.83 inch).

Skin:
*Thickness.*—Thin.
*Texture.*—Firm.
*Tendency to crack.*—None known.
*Blush color.*—Pl.56 J10 — Catawba.
*Ground color.*—Pl.55 L8 — Rubient.
*Pulp.*—Clear.
*Lenticels.*—0.

Flesh:
*Flesh color.*—Pl.46 L10 Romanesque.
*Juice production.*—Very good.
*Flavor.*—Very good.
*Aroma.*—Very mild.
*Texture.*—Firm.
*Ripening.*—Even.
*Eating quality.*—Very good.
*Use.*—Fresh market.
*Keeping quality.*—Very good.
*Resistance to disease.*—Unknown.
*Resistance.*—Unknown.
*Harvest time.*—Mid August to early October.
*Shipping and handling quality.*—Very good.

The above description of a new variety of grapevine is based on the growing conditions near Kerman on the west side of the San Joaquin Valley of Central California. Variations of the usual magnitude such as differences in maturity dates and production may be due to cultural activities such as irrigation, fertilization, pruning, fruit thinning and climatic changes.

What is claimed is:

1. A new and distinct variety of grape plant having characteristics described and illustrated herein.

* * * * *